US00PP20684P2

(12) United States Plant Patent
Griffard et al.

(10) Patent No.: US PP20,684 P2
(45) Date of Patent: Jan. 26, 2010

(54) ***SOLENOSTEMON* PLANT NAMED 'TRE RES 08'**

(50) Latin Name: *Solenostemon scutellarioides*
Varietal Denomination: TRE RES 08

(75) Inventors: Leroy Griffard, Ste. Genevieve, MO (US); Jackie Griffard, Ste. Genevieve, MO (US)

(73) Assignee: Tristar Nursery, Ste. Genevieve, MO (US)

( * ) Notice: Subject to any disclaimer, the term of this patent is extended or adjusted under 35 U.S.C. 154(b) by 0 days.

(21) Appl. No.: 12/220,247

(22) Filed: Jul. 23, 2008

(51) Int. Cl.
*A01H 5/00* (2006.01)

(52) U.S. Cl. ..... Plt./373

(58) Field of Classification Search ..... Plt./263.1, Plt./373

See application file for complete search history.

*Primary Examiner*—Susan B McCormick Ewoldt
(74) *Attorney, Agent, or Firm*—Mark P. Bourgeois

(57) ABSTRACT

A new and distinct *Solenostemon* plant cultivar is disclosed, characterized by deeply lobed, unjulating leaves; a sun tolerant *Solenostemon* that exhibits four colors; a more uniform growth habit; and short internodes.

1 Drawing Sheet

Latin name of the genus and species: *Solenostemon scutellarioides.*

Variety denomination: 'TRI RES 08'.

BACKGROUND OF THE INVENTION

The new cultivar 'TRI RES 08' is a product of a natural mutation. The new cultivar was discovered and selected by Leroy and Jackie Griffard in April 2004 in Ste. Genevieve, Mo. The new cultivar was discovered in a greenhouse in a group of other *Solenostemon* plants but exhibited different leaf coloring and growing characteristics. The exact parent plant is unknown.

Asexual reproduction of the new cultivar 'TRI RES 08' by terminal cuttings was performed in Ste. Genevieve, Mo. and Oxnard, Calif., and has shown that the unique features of this new cultivar are stable and reproduced true to type on successive generations.

SUMMARY OF THE INVENTION

The cultivar 'TRI RES 08' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'TRI RES 08'. These characteristics in combination distinguish 'TRI RES 08' as a new and distinct *Solenostemon* cultivar:

1. Deeply lobed, unjulating leaves;
2. A sun tolerant *Solenostemon* that exhibits four colors;
3. A more uniform growth habit; and
4. Short internodes.

In comparison to the commercially available variety 'Touch of Class' (U.S. Plant Pat. No. 14,392), 'TRI RES 08' is more compact in both height and plant spread. Additionally, the foliage of the new variety 'TRI RES 08' are a darker green and a darker red than the green and red in the foliage of 'Touch of Class'. Further, the markings on the foliage of the new variety 'TRI RES 08' are different in shape than 'Touch of Class.'

BRIEF DESCRIPTION OF THE PHOTOGRAPH

The accompanying photograph in FIG. 1 illustrates in full color a typical plant of 'TRI RES 08' grown in a four-inch pot. One cutting was used in the pot, planted mid December and grown in a greenhouse. During the production of the plants, day temperatures were about 25° C., night temperatures were about 12° C. and light levels ranged from 4,000 to 6,000 footcandles. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'TRI RES 08' plants grown in Oxnard, Ventura County, Calif., during the months of December through February. The growing temperature ranged from 12° C. to 15° C. at night to 12° C. to 20° C. during the day. Measurements and numerical values represent averages of typical *Solenostemon* plants.

Botanical classification: *Solenostemon* cultivar 'TRI RES 08.'

Commercial classification: Coleus.

PROPAGATION

Type cutting: Terminal cuttings.
Time to initiate roots: 4 days with 18° C.
Time to develop roots: 6 to 8 days with 16° C. to 18° C.
Root description: Fine, fibrous, white in color.
Rooting habit: Freely branching.

PLANT

Form: Annual potted or garden plant.
Growth habit: Low and outwardly spreading plant habit.

Growth rate: Rapid; moderately vigorous.
Plant height: About 30 cm.
Plant diameter: About 35 cm.
Branching habit: Freely branching with about nine lateral branches per plant.
Length of Lateral branches: About 15 cm.
Diameter: About 5 cm.
Internode length: About 3 cm.
Strength: Strong.
Aspect: Initially upright then outwardly spreading.
Shape, in cross-section: Squarish.
Texture: Pubescent.
Color: Near Greyed-Purple 183A.

FOLIAGE

Arrangement: Opposite; simple.
Length: About 9.5 cm.
Width: About 6.5 cm.
Shape: Roughly deltoid.
Apex: Broadly acute.
Base: Truncate.
Margin: Crenate; scalloped, ruffled.
Texture:
*Upper surface.*—Lightly pubescent.
*Lower surface.*—Lightly pubescent.
Venation pattern: Pinnate; netted.
Color:
Developing foliage on the upper surface:
*Towards the margins.*—Near Greyed-Purple 187A and 187B.
*Towards the center.*—Near Green 139C.
*Center.*—Near Yellow-Green 154C.
*Towards the base.*—A mix of Green 139C and Greyed-Purple 187B.
*Venation.*—Near Green-Purple 187A.
Developing foliage on the lower surface:
*Towards the margins.*—Near Greyed-Purple 187A and 187B.
*Towards the center.*—Near Green 139C.
*Center.*—Near Yellow-Green 154C.
*Towards the base.*—A mix of Green 139C and Greyed-Purple 187B.
*Venation.*—Near Green-Purple 187A.
Fully expanded foliage on the upper surface:
*Towards the margins.*—Near Greyed-Yellow 162C.
*Towards the center.*—Near Green 139C.
*Center.*—Near Greyed-Purple 187A.
*Towards the base.*—Near Green 139C and Greyed-Purple 187A.
*Venation.*—Near Greyed-Purple 187A.
Fully expanded foliage on the lower surface:
*Towards the margins.*—Near Greyed-Yellow 162C.
*Towards the center.*—Near Green 139C.
*Center.*—Near Greyed-Purple 187A.
*Towards the base.*—Near Green 139C and Greyed-Purple 187A.
*Venation.*—Near Greyed-Purple 187A.
Petiole length: About 3.5 cm.
Petiole diameter: About 0.2 cm.
Petiole color:
*Towards the apex.*—Near Greyed-Purple 187B with shades of near Green 139C.
*Towards the base.*—Near Greyed-Purple 187B.
Flower description: Flower development has not been observed to date.

OTHER CHARACTERISTICS

Disease resistance: Neither resistance nor susceptibility to diseases or pests has been observed in this variety.
Drought tolerance/cold tolerance: Plants of the new *Solenostemon* have been observed to have no drought tolerance and do not produce at a temperature lower than 8° C.
Fruit/seed production: Commercially, this plant is not used or observed in a stage where seeds would be produced. Therefore, seed production has not been observed.

What is claimed is:

1. A new and distinct cultivar of *Solenostemon* plant named 'TRI RES 08' as herein illustrated and described.

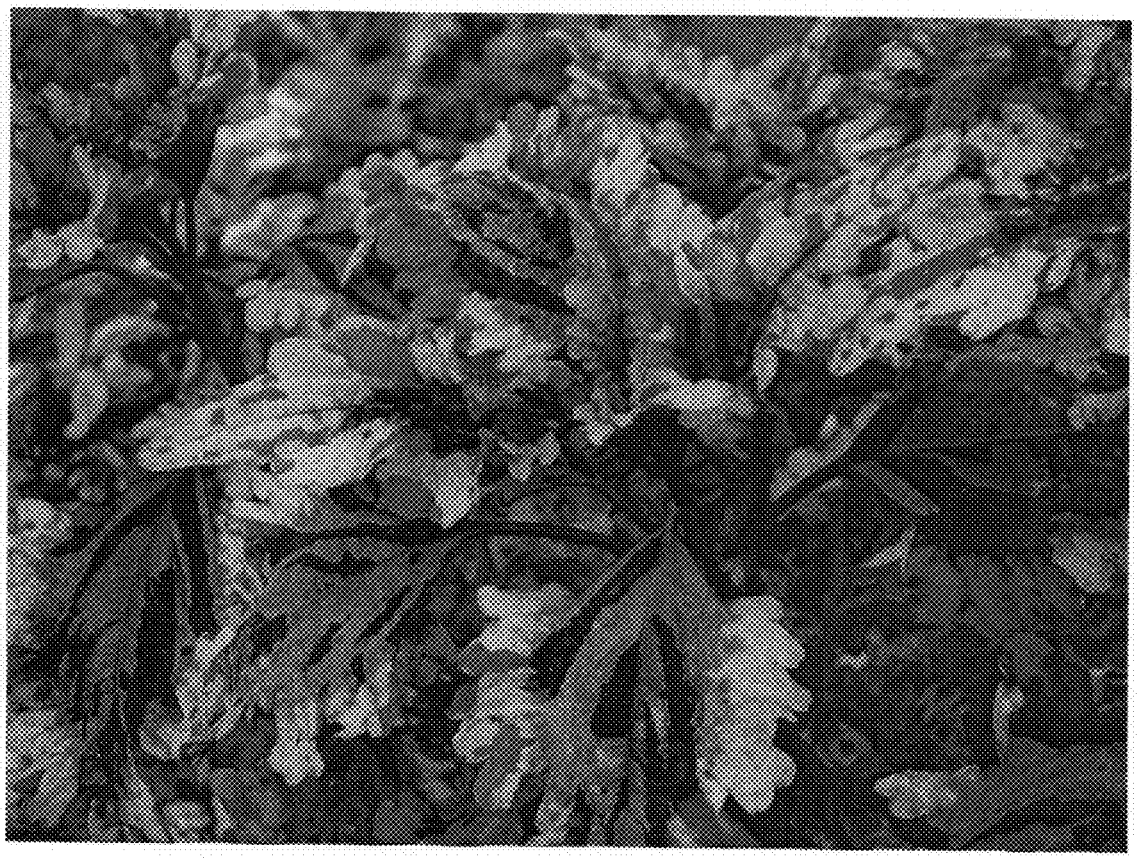

* * * * *